United States Patent [19]

Naumann

[11] 4,337,352
[45] Jun. 29, 1982

[54] SEPARATION OF ENANTIOMERS OF CHIRAL CARBOXYLIC ACIDS

[75] Inventor: Klaus Naumann, Cologne, Fed. Rep. of Germany

[73] Assignee: Bayer Aktiengesellschaft, Leverkusen, Fed. Rep. of Germany

[21] Appl. No.: 263,812

[22] Filed: May 15, 1981

Related U.S. Application Data

[63] Continuation of Ser. No. 43,981, May 31, 1979, abandoned.

[30] Foreign Application Priority Data

Jun. 20, 1978 [DE] Fed. Rep. of Germany ....... 2826952

[51] Int. Cl.³ .................. C07B 19/00; C07B 21/00
[52] U.S. Cl. ................................ 562/401; 562/506
[58] Field of Search ........................... 562/401, 506

[56] References Cited

U.S. PATENT DOCUMENTS

| | | | |
|---|---|---|---|
| 3,590,077 | 6/1971 | Muller | 562/401 |
| 3,666,798 | 5/1972 | Motsui et al. | 562/401 |
| 3,842,125 | 10/1974 | Horiuchi et al. | 562/401 |
| 3,879,451 | 4/1975 | Yoshioka et al. | 562/401 |
| 3,988,365 | 10/1976 | Gallegra | 562/401 |
| 4,014,918 | 3/1977 | Martel | 562/401 |
| 4,016,205 | 4/1977 | Kariyone | 562/401 |
| 4,118,417 | 10/1978 | Epstein | 562/401 |
| 4,182,906 | 1/1980 | Suzukamo | 562/401 |
| 4,229,593 | 10/1980 | Kondo et al. | 562/401 |
| 4,236,026 | 11/1980 | Naumann | 562/401 |

FOREIGN PATENT DOCUMENTS

| | | | |
|---|---|---|---|
| 746726 | 3/1970 | Belgium | 562/401 |
| 747847 | 3/1970 | Belgium | 562/401 |

Primary Examiner—Paul J. Killos
Attorney, Agent, or Firm—Sprung, Horn, Kramer & Woods

[57] ABSTRACT

A process for the separation of enantiomers of a chiral carboxylic acid, comprising reacting an alkali metal salt of the acid with an amount of an optically active amine salt which is equivalent to only one enantiomer, in an aqueous weakly alkaline buffered solution as the reaction medium, the reaction medium having a pH value at which the entire acid is present in the ionized form but at which no amine salt is yet deprotonated. Advantageously the carboxylic acid is of the formula

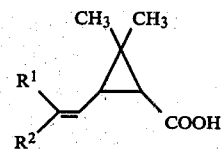

wherein
$R^1$ and $R^2$ each independently is hydrogen, alkyl, with 1–4 C atoms, halogen, optionally substituted phenyl or optionally substituted phenylmercapto, the optically active amine salt is a mineral acid salt of a phenylglycine alkyl ester, α-methylbenzylamine, phenylethylamine, phenylethanolamine, 1-phenyl-2-dimethyl-amino-1,3-propanediol or abietylamine, the buffered solution contains potassium carbonate, sodium carbonate, sodium bicarbonate or sodium hydrogen phosphate as the buffering agent, and the reaction is effected at about 0° to 100° C., the process including the further steps of separating the precipitated ammonium salt from the alkali metal salt that remains in solution, treating the ammonium salt with a strong acid whereby the free carboxylic acid enantiomer is liberated, and treating the alkali metal salt that remains in solution with a strong acid whereby the free carboxylic enantiomer is liberated.

10 Claims, No Drawings

SEPARATION OF ENANTIOMERS OF CHIRAL CARBOXYLIC ACIDS

This is a continuation of application Ser. No. 43,981, filed May 31, 1979, now abandoned.

The present invention relates to an unobvious process for the resolution of racemates of chiral carboxylic acids.

The resolution of racemic carboxylic acids into their enantiomers by reaction with optically active amines and utilization of the differences in energy, which manifests itself in the different physical properties of the diastereomeric compounds thus formed, is a method which has been customary for a long time. In practice, however, there are various unexpected difficulties, which fact renders general applicability of the results of a successful resolution of racemates impossible, even for similar separation problems. Each separation problem requires its individual solution. In this context, Elliel also notes in "Stereochemie der Kohlenstoffverbindungen" ("Stereochemistry of the Carbon Compounds"), Verlag Chemie Weinheim 1966, pages 59–99: "The resolution of racemates is still an art."

It is of particular interest industrially to separate the racemates of the carboxylic acids important for pyrethroid insecticides, since the individual enantiomers display great differences in their action. These separations have hitherto been carried out by fractional precipitation or crystallization of the salts with optically active amines into the particular enantiomers.

The table which follows provides a survey of the attempts for solving the problem of separating racemic carboxylic acids which are important for pyrethroids into their enantiomers:

| Carboxylic acid | Optically active amine | Mol ratio | Solvent | Literature |
|---|---|---|---|---|
| 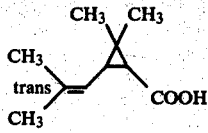 | 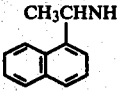 | 1:1 | C$_2$H$_5$OH | Derwent Basic Abstract Journal (BAJ) 13445 W/08 Japanese Application J 4 9,109,344 |
| " | 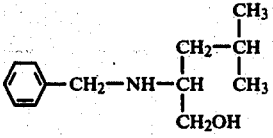 | 1:1 | i C$_3$H$_7$OH | BAJ 15058 W/09 Japanese Application J 4 9,092,049 |
| " | 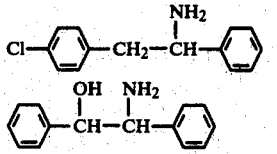 | 1:1 | 20% H$_2$O 80% C$_2$H$_5$OH | BAJ 79586 W/48 Japanese Application J 7 5,034,019 |
| " | 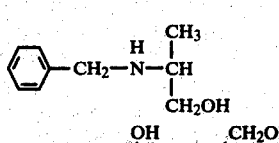 | 1:1 | 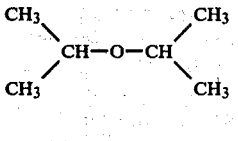 | BAJ 38880 X/21 Japanese Application J 5 1,041,344 |
| " | 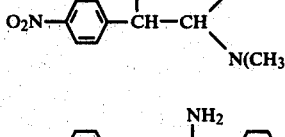 | 1:1 | | Agr. Biol. Chem. 37, 1,713–1,716 (1973) |
| 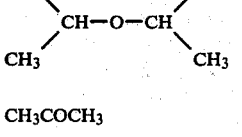 | 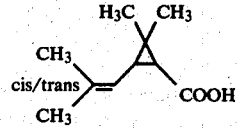 | 1:1 | 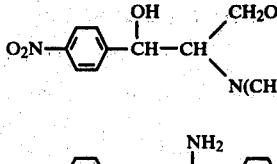 | French Application 1,536,458 |
| 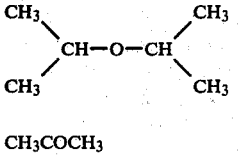 | 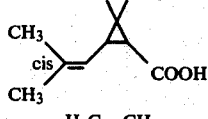 | 1:1 | CH$_3$COCH$_3$ | BAJ 21671 W/13 Japanese Application J 4 9,125,342 |
| 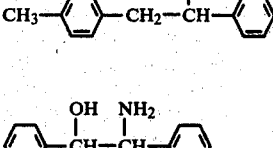 | 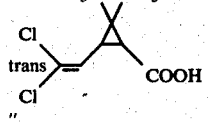 | 1:1 | CH$_3$OH | BAJ 35181 X/19 Japanese Application J 5 1,036,441 |
| " | 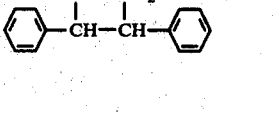 | 1:1 | 50% H$_2$O 50% CH$_3$OH | BAJ 85207 Y/48 Japanese Application J 5 131,953 |
| " | 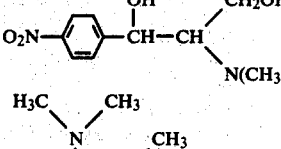 | 1:1 | H$_2$O | BAJ 06690 Y/04 Japanese Application J 5 1,143,647 |

-continued-

| Carboxylic acid | Optically active amine | Mol ratio | Solvent | Literature |
|---|---|---|---|---|
| " | $O_2N$-⟨⟩-CH(OH)-CH(CH$_2$OH)(N(CH$_3$)$_2$) | 1:1 | $CH_3COOC_2H_5$ | DE-OS (German Published Specification) 2,439,177 |
| Cl, Cl, cis, H$_3$C, CH$_3$, COOH (2,2-dichlorovinyl-dimethylcyclopropanecarboxylic acid) | ⟨⟩-CH(NH$_2$)-CH$_3$ | 1:1 | $CH_3COOC_2H_5$ | DE-OS (German Published Specification) 2,549,177 |
| R-⟨⟩-CH(CH(CH$_3$)$_2$)-COOH, R = OCH$_3$, F, Cl, Br | CH$_3$-⟨⟩-CH$_2$-CH(NH$_2$)-⟨⟩ | 1:1 | 40% H$_2$O, 60% C$_2$H$_5$OH | BAJ 45194 W/27 Japanese Application J 5 25,544 |
| CH$_3$-⟨⟩-CH(CH(CH$_3$)$_2$)-COOH | CH$_3$-⟨⟩-CH(CH$_2$NH$_2$)(⟨⟩) | 1:1 | 40% H$_2$O, 60% C$_2$H$_5$OH | BAJ 82419 W/50 Japanese Application J 5 106,935 |
| (CH$_3$)$_3$C-⟨⟩-CH(CH(CH$_3$)$_2$)-COOH | CH$_3$-⟨⟩-CH$_2$-CH(NH$_2$)-⟨⟩ | 1:1,2 1,2 | 20% H$_2$O, 80% C$_2$H$_5$OH | BAJ 10328 X/06 Japanese Application J 5 126,635 |

+This separation was not successful with optically active α-naphthylamine

These processes follow the above-mentioned classical procedure in which equimolar amounts of amine and acid are first reacted and the salt formed is then subjected to fractional crystallization. These processes are troublesome when applied on a large scale because they necessitate many crystallization stages in some cases and usually give the desired enantiomer in unsatisfactory yield. Optically active amines, which are not readily available in relatively large amounts, are required. Furthermore, the amine can be recycled for an industrially useful continuous process only in a complicated manner. These processes are thus unsuitable for overcoming the separation problem on a large scale.

The present invention now provides a process for the separation of enantiomers of a chiral carboxylic acid, which is characterized in that an alkali metal salt of the acid is reacted with an amount of an optically active primary, secondary or tertiary amine salt which is equivalent to only one enantiomer, and in that an aqueous, weakly alkaline buffered solution with a pH value at which the entire acid is present in the ionized form but at which no amine salt is yet deprotonated is used as the reaction medium.

It has furthermore been found that the ester salts which can be obtained smoothly from D-phenylglycine, which is easy to prepare (Japanese application No. J 5 1,095,036), for example (−)-phenylglycine ethyl ester hydrochloride (J. biol. Chem. 135, 91 (1940)), can advantageously be employed for the resolution of the racemates.

In the reaction according to the invention, only one enantiomer is selectively precipitated as the optically active ammonium salt and the other enantiomer remains in solution as the alkali metal salt. The enantiomeric carboxylic acids are liberated with strong mineral acids.

It is surprising that separation of the enantiomers is successful by the process according to the invention, since the solubility differences, which are decisive, for the separation, of the diastereomeric salts could not be foreseen.

The process according to the invention has a number of advantages. Thus, the process is devoid of troublesome fractional crystallizations. Crystallization, which may be necessary, of the enantiomers once separated proves simple, since any racemic constituents still present are usually much more sparingly soluble than the optically pure compounds and can thus be readily separated off in one step.

The process according to the invention is suitable, above all, for isolating relatively large amounts of pure enantiomers. The enantiomers can be liberated directly from the separated salts in a simple manner, it being easily possible to recycle the amine, whereby the process according to the invention can also easily be operated continuously.

If, for example, 2 moles of (±)-trans-2-(2,2-dichlorovinyl)-3,3-dimethyl-cyclopropanecarboxylic acid are used as the starting substance, aqueous sodium bicarbonate solution is used as the alkaline medium, 1 mole of (−)-phenylglycine ethyl ester hydrochloride is used as the optically active amine salt and hydrochloric acid is used as the liberating acid, the course of the reaction can be represented by the equation which follows:

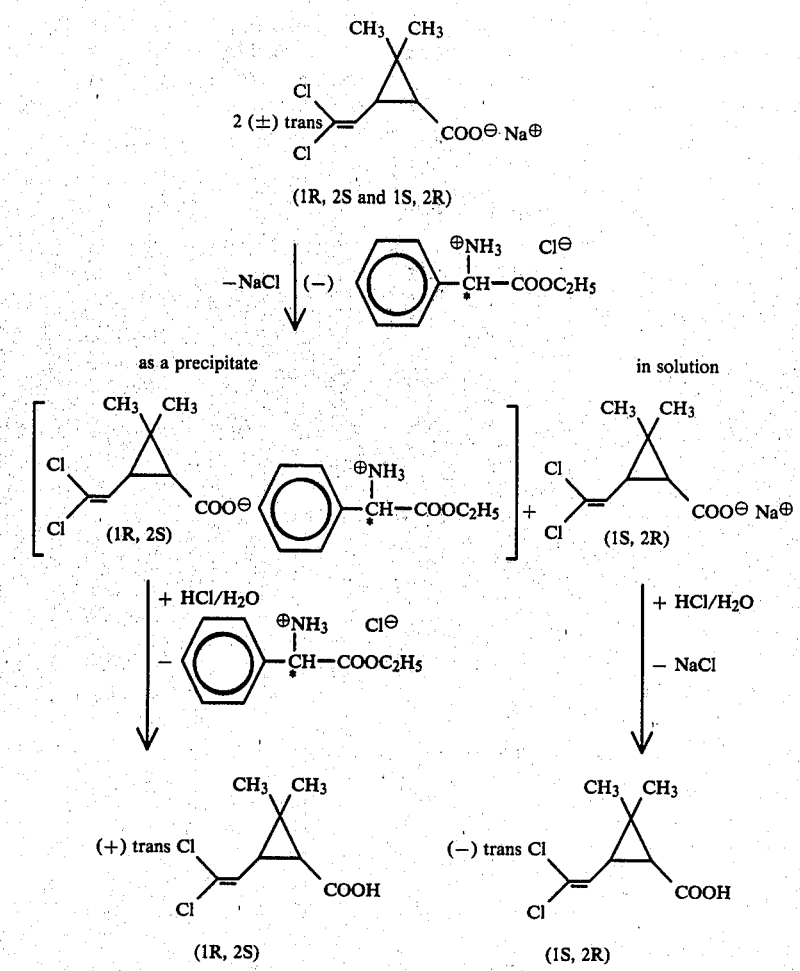

The process according to the invention is preferably used for the separation of chiral carboxylic acids of the general formula

R—COOH  (I)

in which

R represents a substituted cyclopropyl radical or an optionally substituted 1-phenyl-2-methyl-prop-1-yl radical.

The process according to the invention is particularly suitable for the separation of the carboxylic acids of the general formula (I) in which R represents the radical

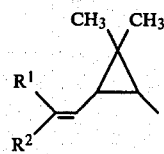

wherein

R¹ and R², which may be identical or different, each represent hydrogen, alkyl with 1-4 C atoms, halogen (especially chlorine or bromine), optionally substituted phenyl or optionally substituted phenylmercapto.

Specific examples which may be mentioned of the carboxylic acids which can be separated into their enantiomers by the process according to the invention are:

(±)-cis- and (±)-trans-2-(2-methylpropenyl)-3,3-dimethyl-cyclopropanecarboxylic acid, (±)-cis- and (±)-trans-2-(2,2-dichlorovinyl)-3,3-dimethyl-cyclopropanecarboxylic acid, (±)-cis- and (±)-trans-2-(2,2-dibromovinyl)-3,3-dimethyl-cyclopropanecarboxylic acid, α-isopropyl-p-chlorophenylacetic acid and (±)-cis and (±)-trans-2-(2-chloro-2-p-chlorophenyl-vinyl)-3,3-dimethylcyclopropanecarboxylic acid.

The racemic free carboxylic acids to be used as starting materials are known (see DE-OS (German Published Specification) No. 2,738,150, DE-OS (German Published Specification) No. 2,439,177 and the literature cited in the above table). These carboxylic acids are preferably employed in the form of their alkali metal salts.

Optically active amines in the form of their mineral acid salts are used for the process according to the invention. Examples of amines which may be mentioned are the alkyl esters of phenylglycine (especially the lower alkyl esters, particularly methyl or ethyl), and α-methylbenzylamine, phenylethylamine, phenylethanolamine, 1-phenyl-2-dimethylamino-1,3-propanediol and abietylamine.

The process according to the invention is carried out in the presence of buffer substances which maintain a constant, weakly alkaline medium with a pH value at which the entire acid is present in the ionized form but at which no amine salt is yet deprotonated. Aqueous solutions of inorganic salts of polybasic acids, for example of phosphoric acid and carbonic acid, are preferably used for this purpose. Preferred salts include potassium carbonate, sodium carbonate, sodium bicarbonate and sodium hydrogen phosphate.

In the process according to the invention, the enantiomeric carboxylic acids may be liberated by adding strong acids. Preferred acids are inorganic acids, such as hydrochloric acid or sulphuric acid, or organic acids, such as trifluoroacetic acid or trichloroacetic acid.

In carrying out the process according to the invention, the amount of an optically active amine salt corresponding to the proportion of one enantiomer, and preferably an at least molar amount of the buffer substance are used per mole of racemic carboxylic acid. It is not harmful to use slightly less than the equivalent amount of optically active amine salt. The reactants are preferably brought together at between about 0° C. and 100° C. When they are brought together while hot, the mixture is left to crystallize out slowly, and when they are brought together in the cold, the components are combined slowly, whereupon precipitation occurs immediately.

While the amine salt of one enantiomer precipitates as the sparingly soluble component, the alkali metal salt of the other enantiomer remains in solution. The free optically active acid may in each case be liberated from the appropriate salt, in a highly concentrated to optically pure form, by adding the necessary amount of strong acid. The aqueous solution of the optically active amine salt thereby formed again can be re-used directly for a renewed precipitation. If appropriate, the optical purity of enantiomers which are not completely separated can be increased by recrystallization, whereupon the residual racemic constituent can usually be easily separated off as the more sparingly soluble constituent and be re-introduced into the separation.

Suitable solvents for the recrystallization are non-polar solvents, such as alkanes with up to 10 carbon atoms, petroleum ether and cyclohexane, and halogenoalkanes, such as carbon tetrachloride, and also strongly polar solvents, such as aqueous alcohols, ketones and ethers.

In a particular embodiment of the process according to the invention, the residual portion of the undesired enantiomer in an optically impure carboxylic acid separated off by precipitation with an optically active amine can optionally be separated off by a process analogous to the above precipitation, by adding to the weakly alkaline aqueous solution of the alkali metal salt of this optically impure acid an amount, equivalent to the residual amount of enantiomer, of the same optically active amine, this time having the opposite absolute configuration.

The pure optically active carboxylic acids obtained by the process according to the invention are used for the preparation of highly active insecticides of the pyrethroid type.

The examples which follow illustrate the process according to the invention, without indicating a limitation with regard to the extent of its applicability.

EXAMPLE 1

A solution of 0.5 mole of 92% optically pure ($[\alpha]_D^{20}=-91°$ (1% strength solution in water)) (−)-phenylglycine ethyl ester hydrochloride in 1,000 ml of water was added dropwise to 1 mole of (±)-trans-2-(2,2-dichlorovinyl)-3,3-dimethylcyclopropanecarboxylic acid and 1 mole of sodium carbonate in 10 liters of water at 20° C., while stirring. The precipitate which formed was filtered off with good suction, washed with cold water and decomposed by adding 1,000 ml of 0.25 molar sulphuric acid and 1,000 ml of ether at 20° C. The organic phase was separated off, dried and concentrated. (+)-trans-2-(2,2-Dichlorovinyl)-3,3-dimethylcyclopropanecarboxylic acid with an optical purity of 87% was obtained in 95% yield. By recrystallization from petroleum ether and after separating off the residual, more sparingly soluble racemate constituent, the optically pure (+)-trans-acid with an optical rotation of $[\alpha]_D^{20}=+36.0°$ (1% strength solution in chloroform) was obtained.

On appropriate working-up, the (−)-trans-2-(2,2-dichlorovinyl)-3,3-dimethylcyclopropanecarboxylic acid with an optical rotation of $[\alpha]_D^{20}=-36.0°$ (1% strength solution in chloroform) was obtained from the aqueous phase.

EXAMPLE 2

The same procedure as in Example 1 was followed with α-isopropyl-p-chlorophenylacetic acid. Using an 87% optically pure (−)-phenylglycine ethyl ester salt, a precipitate was obtained which contained the (−)-enantiomer of the carboxylic acid with an optical purity of 75%. $[\alpha]_D^{20}=-36°$ (C=1, CHCl₃) (according to DE-OS (German Published Specification) No. 2,737,297, the optical rotation of optically pure (−)-S-α-isopropyl-p-chlorophenyl-acetic acid is $[\alpha]_D^{20}=-48.3°$ (CHCl₃)). The racemic acid crystallized first from petroleum ether, and an acid, of which a high proportion was optically active, remained in solution.

It will be appreciated that the instant specification and examples are set forth by way of illustration and not limitation, and that various modifications and changes may be made without departing from the spirit and scope of the present invention.

What is claimed is:

1. A process for the separation of enantiomers of a chiral carboxylic acid of the formula

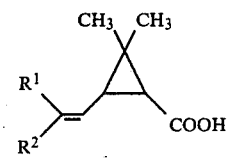

wherein

R¹ and R² each independently is hydrogen, alkyl with 1–4 C atoms, halogen, optionally substituted phenyl or optionally substituted phenylmercapto, comprising reacting an alkali metal salt of the acid with an amount of an optically active phenylglycine ethyl ester salt which is equivalent to only one enantiomer, in an aqueous weakly alkaline buffered solution as the reaction medium, the reaction medium having a pH value at which the entire acid is present in the ionized form but at which no amine salt is yet deprotonated, whereby the ammonium salt of the one enantiomer precipitates while the alkali metal salt of the other enantiomer remains in solution, and separating the precipitate from the solution.

2. A process according to claim 1, wherein the optically active amine salt is a mineral acid salt of a phenylglycine alkyl ester, α-methylbenzylamine, phenylethylamine, phenylethanolamine, 1-phenyl-2-dimethylamino-1,3-propanediol or abietylamine.

3. A process according to claim 1, wherein (−)-phenylglycine ethyl ester hydrochloride is used as the salt.

4. A process according to claim 1, wherein the buffered solution contains potassium carbonate, sodium carbonate, sodium bicarbonate or sodium hydrogen phosphate as the buffering agent.

5. A process according to claim 1, wherein the reaction is effected at about 0° to 100° C.

6. A process according to claim 1, wherein the carboxylic acid is of the formula

R—COOH in which

R is a substituted cyclopropyl radical or an optionally substituted 1-phenyl-2-methyl-prop-1-yl radical.

7. A process according to claim 6, in which

R is

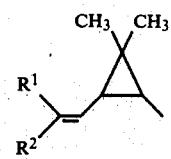

wherein $R^1$ and $R^2$ each independently is hydrogen, alkyl with 1-4 C atoms, halogen, optionally substituted phenyl or optionally substituted phenylmercapto.

8. A process according to claim 1, including the further step of treating the ammonium salt with a strong acid whereby the free carboxylic acid enantiomer is liberated.

9. A process according to claim 1, including the further step of treating the alkali metal salt that remains in solution with a strong acid whereby the free carboxylic acid enantiomer is liberated.

10. A process according to claim 1, wherein the buffered solution contains potassium carbonate, sodium carbonate, sodium bicarbonate or sodium hydrogen phosphate as the buffering agent, and the reaction is effected at about 20° C., the process including the further steps of separating the precipitated ammonium salt from the alkali metal salt that remains in solution, treating the ammonium salt with a strong acid whereby the free carboxylic acid enantiomer is liberated, and treating the alkali metal salt that remains in solution with a strong acid whereby the free carboxylic acid enantiomer is liberated.

* * * * *